Dec. 16, 1947. R. G. BAXTER Plant Pat. 769
SAINTPAULIA PLANT
Filed Jan. 16, 1947
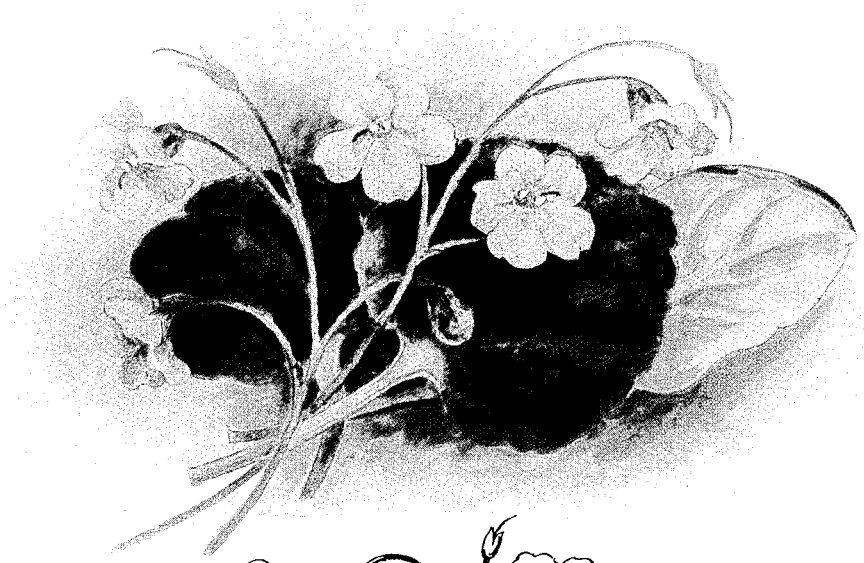
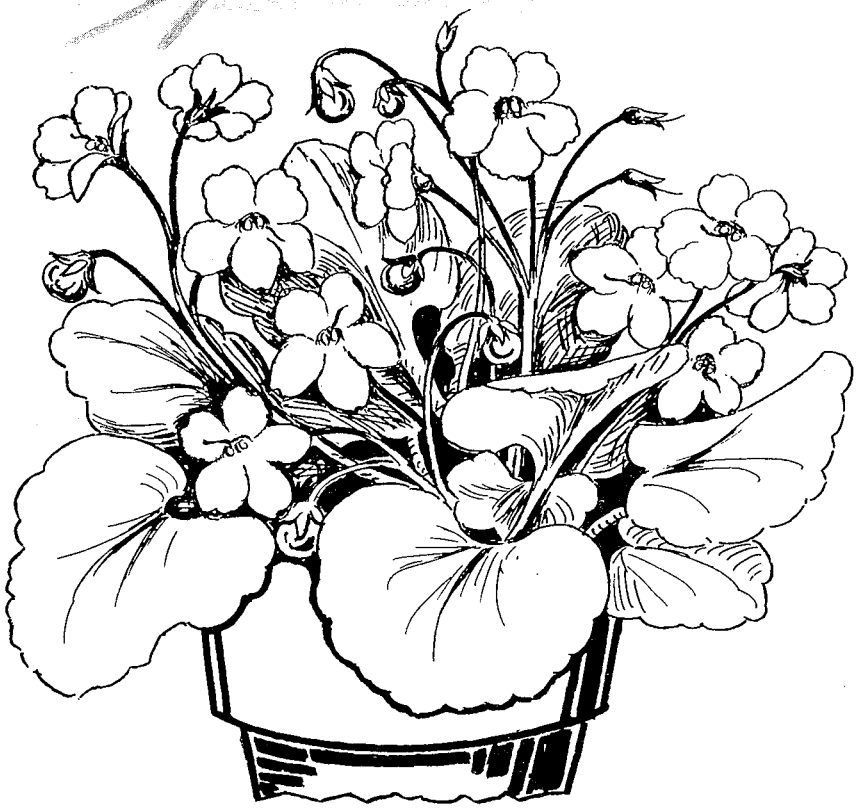
WITNESS
Addison J. Avery
INVENTOR
Roy G. Baxter,
Rummler & Rummler & Davis,
ATTYS.

Patented Dec. 16, 1947

Plant Pat. 769

UNITED STATES PATENT OFFICE

769

SAINTPAULIA PLANT

Roy G. Baxter, Youngstown, Ohio

Application January 16, 1947, Serial No. 722,331

1 Claim. (Cl. 47—60)

The present discovery relates to a new and distinct variety of *Saintpaulia ionantha* grandiflora (Hort.) plant which originated as a sport of "Pink Beauty" (Plant Pat. #514).

Asexual reproduction of this new variety by cuttings, since September 1944, has shown its qualities to be permanently fixed.

The primary object in carrying out this invention was to establish the distinctive, deep pink, uniform coloring and form of the cup-shaped flowers. This new variety is distinguishable from the parent plant mainly by this cup-shaped appearance and color of the blooms; by the larger size and slightly ruffled margins of the two upper petals; the cream-colored spot at the axil of each leaf, and the color of the ribs on the underside of the leaves.

The accompanying illustration shows in its upper part, in full color, a cluster of flowers and leaves, and below, a pen and ink sketch of a single potted plant.

In structure this new variety is similar to "Pink Beauty" and "Ulery's Blue Girl" (Plant Pat. No. 535), combining some of the desirable characteristics of both. Its leaf is heart-shaped with round-crested serrated edges, sturdy upstanding petioles, which are heart-shaped in cross-section, and which carry the leaf above the pot and prevent it from bending downward—except as the leaf ages. The leaf is of a uniform green color with a cream-colored spot at the base of each leaf. A pair of veins of red run along and emphasize the ridges on the upper side of the petioles formed by its heart-shaped section, and these spread apart to merge with the edges of the leaf. The new variety has the free-blooming habit of "Ulery's Blue Girl." Like "Pink Beauty," the flowers are borne in a loose cyme, and have a wide-campanulate five-lobed corolla with small calyx; and exserted yellow stamens.

In contrast to "Pink Beauty," the two uppermost petals of this new variety are larger, have slightly ruffled edges, and have a tendency to curve inward to a greater extent filling in the space subtending the three lower petals, thus giving the bloom a cup-like, fuller appearance. The slight decurving of the two upper petals of "Pink Beauty" foreshortens the appearance of the flower, whereas in this new variety these appear larger, have slightly ruffled margins and less space between these two upper petals and the remaining ones.

Another novel feature of this new variety is the long dark pink-colored style growing from the flower tube, which makes a pleasing contrast with the deep yellow of the stamens and the lighter shade of pink of the bloom.

The following is a detailed description of this new variety:

Parentage: Sport.

*Parent variety.*—"Pink Beauty" (Plant Pat. #514).

*Classification*, botanic.—*Saintpaulia ionantha* grandiflora (Hort.).

*Flower*

Blooming habit: Recurrent.

*Bud.*—*Size*—⅛ inch to ¼ inch. *Form*—gamosepalous. *Color* — yellowish - green. *Sepals*—usually 5. *Shape*—pointed. *Calyx*—size; $\frac{3}{16}$ inch to ¼ inch; 5 lobed.

*Bloom.*—*Size*—1⅛ inches to 1¼ inches. *Form*—short tubed, campanulate corolla with 5 ovate lobes; lower 3, large; upper 2, smaller. *Borne*—cymose inflorescence. *Stems*—slender; length: 1 inch to 1¼ inches, peduncles joined to 3 inch to 4 inch stalk of cyme. *Discoloration*—none. *Texture*—silky. *Affected by wet or hot weather*—not "noticeably." *Persistence*—Deciduous. *Fragrance*—none. *Disease resistance*—no common diseases. *Lasting quality*—good; on plant 1 week to 10 days.

Genital organs:

*Stamens, anthers.*—2-celled; length, $\frac{1}{16}$ inch; number, 2.

*Color.*—Yellow.

*Arrangement.*—Opposite and attached by filament to corolla tube.

*Pollen.*—Color—yellow.

*Styles.*—Number, one; length, ½ inch.

*Stigma.*—Inconspicuous.

*Ovaries.*—Superior.

Fruit:

*Shape.*—2-valved oblong capsule.

*Color at maturity.*—Green, changing to brown.

*Plant*

Form: Sub-acaulescent. Height—6 inches.

Foliage:

*Quantity.*—12 to 24 in rosette.

*Color.*—New foliage—light green. Old foliage—darker green.

*Size of leaf.*—Up to 2 inches long and 2¼ inches wide.

*Shape.*—Isodiametric, cordate.

*Texture.*—Pubescent. Upper surface uniformly covered with short white hairs, lower surface glossy and ribbed.

*Petiole.*—Sturdy, 2½ inches long with nearly round cordate section.

The color designations according to "A Dictionary of Color by Maerz and Paul", are as follows:

| | Plate | Letter | No. |
|---|---|---|---|
| Main flower color | 49 | C | 5 |
| Small area at very center | 49 | J | 7 |
| Style | 49 | J | 7 |
| Stamens | 10 | L | 2 |
| Main body of leaf | 22 | L | 7 |
| Back of leaf | 17 | B | 2 |
| Large veins on back of leaf | 17 | B | 5 |
| Peduncles | 5 | D | 9 |

This new variety of Saintpaulia is easily distinguished from other varieties by its deeper pink coloring, its cup-shaped and fuller blossom, its thick sturdy petioles, the upstanding appearance of both the peduncles and petioles, the cream-colored spot at the base of each leaf, and the pleasing contrast in shades of green of the top and underside of the leaf.

Having thus disclosed the invention, I claim:

A new and ornamental variety of Saintpaulia plant characterized particularly by the cup shape of its blooms and the deep pink coloring of its petals; sturdy upstanding petioles; the cream-colored spot at the axil of each leaf, and the slightly ruffled margins of the two upper petals, substantially as described.

ROY G. BAXTER.